United States Patent

Swords et al.

[11] Patent Number: 5,876,435
[45] Date of Patent: *Mar. 2, 1999

[54] COUPLING FOR POROUS RESIN ORBITAL IMPLANT AND OCULAR PROSTHESIS

[75] Inventors: Gregory Swords, Atlanta, Ga.; John W. Shore, Concord, Mass.

[73] Assignee: Porex Surgical Inc., College Park, Ga.

[*] Notice: This patent issued on a continued prosecution application filed under 37 CFR 1.53(d), and is subject to the twenty year patent term provisions of 35 U.S.C. 154(a)(2).

[21] Appl. No.: 700,108

[22] Filed: Aug. 20, 1996

[51] Int. Cl.⁶ ............................................. A61F 2/14
[52] U.S. Cl. ..................................................... 623/4
[58] Field of Search ...................................... 623/4

[56] References Cited

U.S. PATENT DOCUMENTS

| | | | |
|---|---|---|---|
| 2,574,750 | 11/1951 | Moore | 623/4 |
| 2,810,134 | 10/1957 | Radin | 623/4 |
| 5,466,258 | 11/1995 | Rubin | 623/4 |
| 5,571,139 | 11/1996 | Jenkins, Jr. | 606/73 |

FOREIGN PATENT DOCUMENTS 406217999  8/1994  Japan ........................................ 2/14

Primary Examiner—David J. Isabella
Assistant Examiner—John M. Black
Attorney, Agent, or Firm—Lane, Aitken & McCann

[57] ABSTRACT

An improved coupling method and device for an ocular prosthesis to a porous polyethylene implant is provided. According to the invention, a small surgical screws having a domed head is inserted into a porous plastic implant after the implant has been implanted into an enucleated orbit allowed to vascularize. The domed head projects from the anterior surface of the implant which is covered by conjunctive tissue and is received by a complementary cavity on the rear surface of the ocular prosthesis.

16 Claims, 2 Drawing Sheets

COUPLING FOR POROUS RESIN ORBITAL IMPLANT AND OCULAR PROSTHESIS

SUMMARY OF THE INVENTION

The present invention relates to orbital implants and more specifically to the connection or integration of orbital implants to ocular prosthesis. The invention involves driving a uniquely designed surgical grade titanium screw within a porous resin ocular implant which has been allowed to vascularize. A domed head of the screw extends from the anterior surface of the implant and serves as a ball on which an ocular prosthesis is coupled. The ocular implant used to fill the orbit is formed of porous polyethylene such as a MEDPOR® surgical implant biomaterial which has been approved by the FDA for use as ocular reconstruction implants.

BACKGROUND OF THE INVENTION

After enucleation or evisceration of an eye, surgeons will routinely fill the void with an implant material to prevent the eye socket and surrounding tissue from collapsing and to provide support for a natural looking prosthesis. Over the years a wide variety of materials have been employed as orbital implants including gold, silver, vitallium, platinum, aluminum, cartilage, bone, fat, fascia, lata, sponge, wool, cork, rubber, silk, catgut, peat, agar, asbestos, ivory, paraffin and cellulose. More recently, surgeons have usually replaced the orbital contents of an enucleated eye with either glass, metal, silicone, methylmethacrylate, autogenous tissue or hydroxyapatite. Although each of these materials satisfactorily filled the orbit cavity and thereby supported the neighboring tissues, many of the materials available in the prior art had disadvantages. Prior art materials and methods designed to meet these objectives and criteria were plagued with problems including loss of eye movement, migration (implant drifting), extrusion (Implant rejection), poor movement of the prosthesis and drooping of the lower eyelid. Sterile hydroxyapatite, which can be obtained from coral or by synthetic means, has been a relatively successful material and was approved by the FDA for such surgeries in the 1980's.

After an eye is removed because of trauma, disease, pain, cosmesis or tumor, it is desirable to reconstruct the orbital area and replace the ocular area with a natural looking prosthesis to simulate the look of the eye. The custom external prosthesis, typically made from methylmethacrylate, are designed by ocularists who fit the prosthesis to the patient and decorate the external surface to realistically match the remaining healthy eye of the patient. In order for the prosthesis to appear realistic it is desirable to have the prosthesis track the movement of the remaining lateral or real eye. In this regard, some success has been achieved in attachment of the extraocular muscles which control movement of the eye to the implant which fills the orbit. After attachment of the muscles the orbital implant will mimic the motion of the remaining functional eye. In order to better translate the movement of the orbital implant to the prosthesis, the components can be coupled or linked together.

In addition to the motility function, the orbital implant supports the surrounding tissues and allows for placement of a natural looking prosthetic for the eye. One problem with prior ocular implants is that the eye socket would often appear to recede or sink back. The condition, characterized by an implant having a sunken appearance caused by the shrinking or sinking back of the eye socket, is referred to as enophthalmos. Efforts directed at mitigating enophthalmos of the anophthalmic socket have often resulted in limiting the motility of the implant and increasing pressure on the lower eyelid.

In connection with hydroxyapatite implants, one manner disclosed in the prior art to couple and secure the prosthesis to the orbital ocular implant involves providing the orbital implant with a post or projection on which the prosthesis is received by a complementary opposite depression or cavity provided thereon. The use of a ball and socket or peg coupling mechanism also helps to support the ocular prosthesis and thus can relieve pressure on the lower eyelid by supporting some of the weight of the prosthesis. In this regard some patients have been able to rectify a problem by a drooping lower lid using a direct coupling method. The post or peg is inserted into a bore hole which is drilled into the anterior surface of the orbital implant after it has been implanted and allowed to significantly vascularize. The post is retained within the bore hole by frictional engagement and eventually tissue grows along the sidewalls of the bore hole adjacent to the peg. The opposite end of the post, which extends outwardly from the anterior surface of the implant, is received in an opposite bore hole or cavity provided on the rear of the in the ocular prosthesis. The prior art also discloses inserting a cylinder having threads on the exterior surface of the cylinder and a smooth bore hole which can receive a peg or post. The prior art further discloses additional manners in which to couple implants with ocular prosthesis which are made from other materials. For example, some involve providing integral projections on either the orbital implant or the ocular implant which can be received by an opposite cavity and intended to be permanently secured. Others have taught the use of magnetic couplings between the prosthesis and the orbital implant. Due to excessive infection and extrusion rates, the use of such coupling systems have been, by in large, abandoned. The introduction of porous hydroxyapatite implants effectively mitigated many of the problems involving infection, extrusion and migration. The introduction of porous implants provided the opportunity for the ocular implant to allow for the ingrowth of vascular tissues into the porous surface of the implant. These materials have diffuse and small pores which allow the blood vessels and tissue to grow into them making them an integral part of the body. Vascularization of the implant minimizes the problems of migration and extrusion. Because non-porous implants have a higher incidence of failure due to infection and complications, porous implants are favored. Although hydroxyapatite is resistant to infection, under experimental conditions it has been established that the material interfered with normal host tissue response and led to chronic mild inflammation that did not completely resolve. Some additional drawbacks to the hydroxyapatite material are that it is abrasive, relatively heavy and must be carved from its natural state to conform to the shape and size of the orbital void. Furthermore, hydroxyapatite is relatively brittle and fragile and due to these inherent mechanical properties it was difficult to mechanically attach ocular muscles to the implant and provide a linkage to the prosthesis. The manners in which to couple the orbital implant to the prosthesis were limited to the post system described above.

Integration of the coupling link from the implant to prosthesis requires the patient to undergo a second operation after the orbital implant has been implanted, healed and become vascularized. During the second operation a hole is drilled at a location determined to align with the center of the eye. In order to minimize trauma to the conjunctiva which has grown over the implant surface, it is best to use a drill bit with the cutting portion limited to the ends of the bit and not up the sides is used. In the prior art, a post having a diameter of 2.5 mm was fitted within a 3 mm diameter hole. According to prior art methodology, a hole was drilled into the implant which required drilling into the brittle implant material to a depth of approximately 14 mm. This operation created drilling fragments and powder which was then removed. After the bore hole is formed, tissue is provided to line the interior confines of the bore hole. In the alternative, since the exterior region of the implant is invested with blood vessels and fibrous tissues which will support epithelial growth, epithelial tissue will grow down the sides of the drilled hole during a second healing process.

Although the results of this prior art procedures have generally been favorable, there have been reports of granulation tissue growth occurring within the central hole which pushes out the motility peg. Such growth, when it occurs, can be prolific requiring repeated excisions and repositioning of the peg. Because the motility peg is not secured to the implant, it is possible to lose the motility peg during cleaning of the prosthesis. Further, the method involves imposing significant additional trauma to the tissues which have grown into the orbital implant. In view of the complications which were raised, in some cases, integration of the prosthesis and implant was avoided.

Although the use of porous hydroxyapatite provided a number of advantages over the prior art materials used for orbital implants problems as described above continued to exist. During the 1980's porous plastic implants of a surgical grade polyethylene were developed which had a number of advantages over hydroxyapatite. These implants have superior strength, were light weight, and have proven to be effective in many of the applications which had been previously performed by hydroxyapatite materials. Porex Surgical of College Park, Ga. manufactures such implant materials under the trademark MEDPOR® and markets products designed for implantation into the anophthalmic socket identified as MEDPOR® spheres and the MEDPOR® CVA (conical volume augmentation) ocular implant. Porous polyethylene is an inert material which has the same advantages afforded by the porous surfaces provided by naturally occurring hydroxyapatite. The plastic is inert, stable and easily can be sterilized. Because the implant is synthetic, an uninterrupted supply of the material is readily available. Further, the material can be easily molded and shaped to appropriately fit an orbital void which requires an implant. Lastly, because the porous material is flexible and pliable, it enabled surgeons to employ new coupling methods between the implant and the ocular prosthesis and between the implant and the extraocular muscles. While hydroxyapatite may be brittle and can crack at the interface between a screw and the implant material, porous polyethylene can be compressed.

SUMMARY OF THE INVENTION

The present invention provides an improved coupling method for porous resin implants for the anophthalmic sockets and ocular prosthesis. The linkage is effected by a coupling screw wherein the shank of the screw is retained within the orbital implant. The head of the screw engages an opposite socket provided on the ocular prosthesis. The unique properties of the orbital implant material make the use of such a screw possible and effective. In contrast, the prior art implants were not receptive to such a coupling because a screw could crack or fracture the implant. The screw coupling device and method as described has a number of advantages over the prior art coupling arrangements. The very small shank of the screw allows for the use of minimally invasive pilot hole which minimizes trauma to conjunctiva and underlying tissues. The screw is designed with a variable thread width for secure anchoring. The threads are likewise deep cutting and self tapping and are thus are optimally designed to purchase in porous polyethylene material which has the necessary strength and resiliency to securely hold the coupling screw. Because porous polyethylene can be compressed at the interface between the orbital implant and the screw threads, the ability of the screw to be securely held within the implant is enhanced. The head of the coupling screw further supports part of the weight of the prosthesis and thereby reduces pressure on the lower eyelid. An implant which is appropriate for use in connection with the screw is fully disclosed in U.S. Pat. No. 5,466,258 to Rubin. In an alternative the porous polyethylene implant can be formed in the shape of a sphere. The porous nature of the implant, which provides for vascularization, permits the use of a coupling screw with a reduced risk of infection and extrusion.

DETAILED DESCRIPTION OF THE INVENTION

Figure 1:
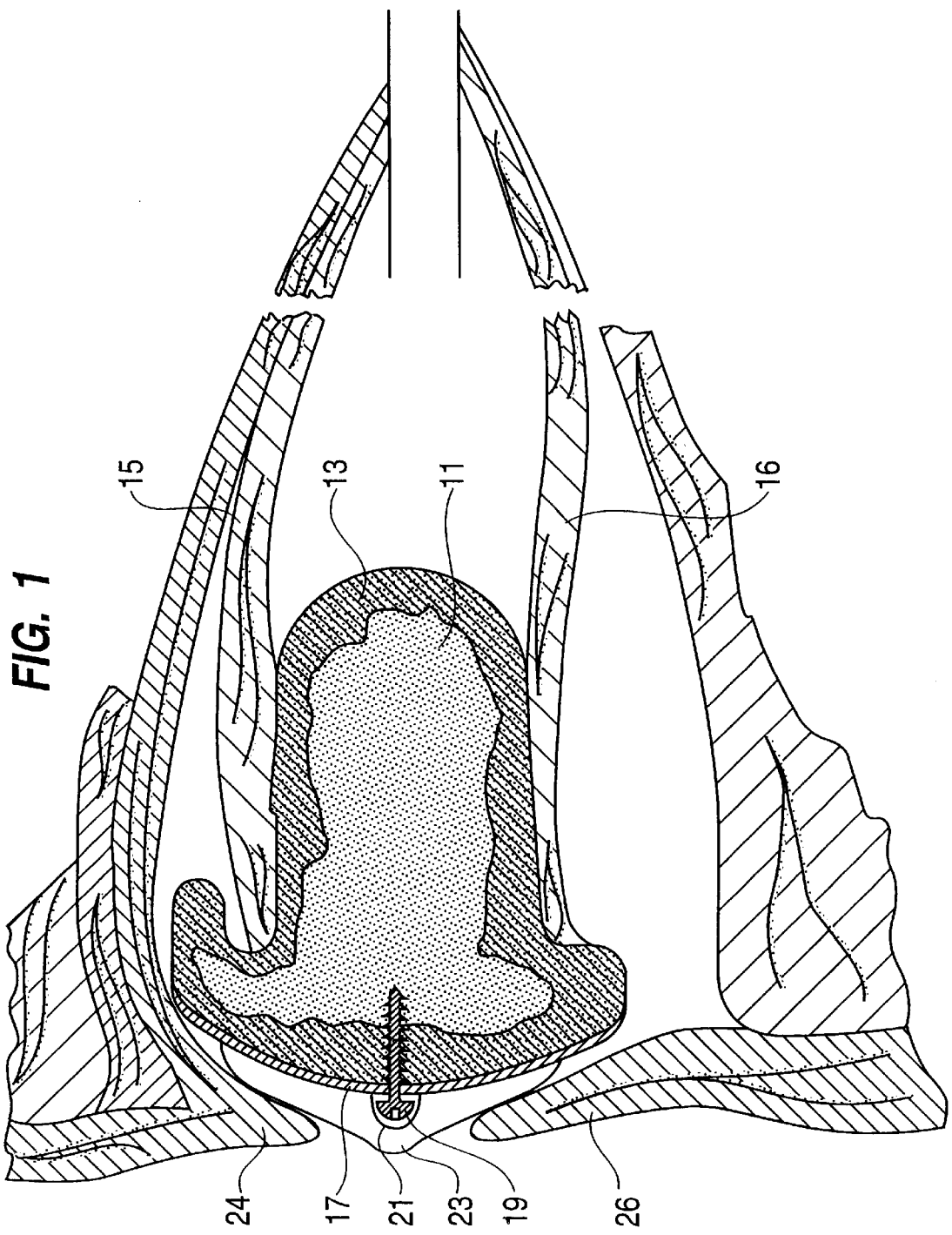
FIG. 1 is a side sectional view of the coupling of an orbital implant with an external prosthesis according to the invention.

Referring now to FIG. 1, a porous polyethylene implant 11 is shown implanted into an anophthalmic socket approximately 3 months after the implantation procedure. An exterior region 13 of implant 11 is shown vascularized with tissue ingrowth from the patient which extends to a depth of approximately 6 mm around the entire implant. Tissue has also grown adjacent to extra-ocular muscles, the superior rectus muscle 15 and the inferior rectus muscles 16 which were attached to implant 11 during the initial surgery. The tissue ingrowth serves to strengthen the interface between the muscles and the implant. On the anterior surface of orbital implant 11 is a layer of conjunctiva tissue 17 approximately 2 mm thick. A surgical grade screw 19 extends through the conjunctiva and into the exterior vascularized region 13 of implant 11. The domed head of screw 19 is shown engaged to a cavity or socket 21 provided on the rear of external prosthesis 23. The prosthesis is held in place by the domed head of the screw, the upper eyelid 24 and the lower eyelid 26.

Figure 2:
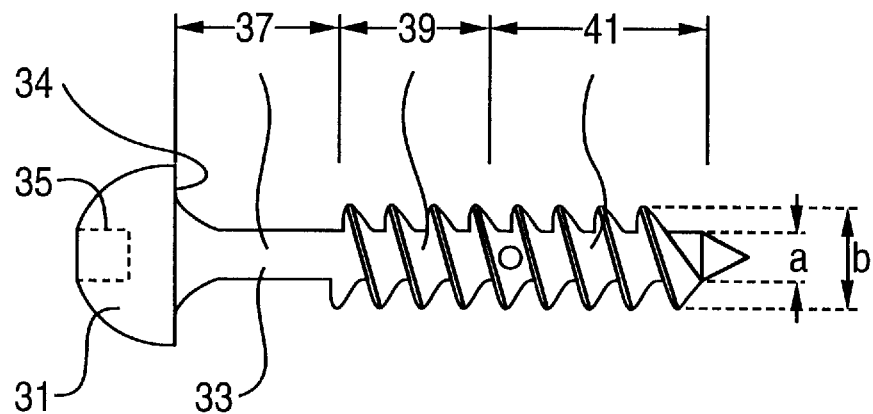
FIG. 2 is a side view in elevation of an ocular screw according to the invention for coupling an external prosthesis to an porous resin implant.

FIG. 2 illustrates a screw according to one embodiment of the invention generally designated by reference numeral 19. Screw 19 is preferably made of #614-4V ELI titanium which meets ASTM standard F136-92. The screw is comprised of a head section 31 which is generally domed and a shank 33. Provided in the center of the head is a square hole 35 having a depth of 0.030 inches from the surface of the domed head. The hole is designed to be engaged by a driver having a bit with a square profile. The shank of the screw has a proximal first section 37 which is devoid of threads and extends from the rear surface 34 of the head for a distance of 0.120 inches. This proximal section of the screw has a diameter of 0.037 inches and, when in position within the implant extends through the conjunctiva. Adjacent to proximal section 37 is medial section 39 which extends 0.10 inch in a distal direction. This medial section has a thread pitch of 0.040 inches. At the end of shank 33 is a distal section 41 which is approximately 0.1 inch long and characterized by threads which have a pitch of 0.033 inches. As described, the screw has a variable thread pitch and is self-tapping. The diameter a of the shank is approximately 0.037 and remains constant throughout its length. On the segment of the shank which has threads, the diameter b of the screw has a maximum dimension of 0.076 inches.

Figure 3:
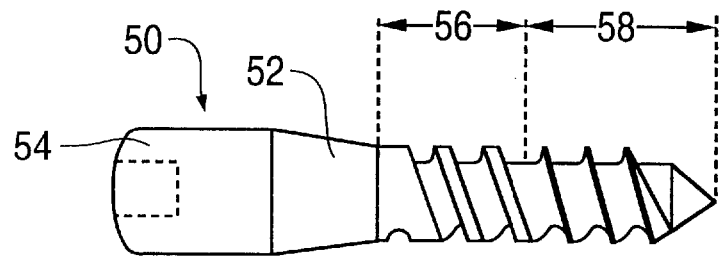
FIG. 3 is a side view in elevation of a second embodiment of a screw which can be used in accordance with the invention.

FIG. 3 depicts an alternative embodiment of the coupling screw generally designated by the reference numeral 50. In this embodiment the screw is made of titanium 6AL-4V ELI and passivated per ASTM F-86-91. In this embodiment, a tapered section 52 connects a head portion 54 of the screw directly to the exterior circumference of the threads formed on the shank. This tapered section is approximately 0.08 inches long. The shank of the screw has a minimum diameter of approximately 0.05 inches and the threads have an outer diameter of 0.076 inches. As with the first embodiment, the threads in the second embodiment have a variable pitch arrangement. A first segment 56 of the shank of the screw has a distance of 0.123 inches and a thread pitch of 0.040 inches. A second segment 58 of the shank has a distance of approximately 0.135 and has a thread pitch of 0.135 inches. In the second embodiment the axial length of the head of the screw available to engage the ocular implant is 0.12 inches and thus slightly larger than the length of the head of the screw disclosed in the first embodiment. Further, the thickness or width of the threads are larger in the first segment in this embodiment.

The coupling procedure according to the invention proceeds after a routine enucleation or evisceration of the eye by an ophthalmologist or oculoplastic surgeon. The orbit is filled during this initial operation with a surgical implant made of porous polyethylene such as that sold by Porex Surgical of College Park, Ga. and described above. Referring back to FIG. 1, the implant 11 is inserted into the patient's remaining scleral sac from which the cornea has been removed and uveal tissue eviscerated. The surgeon may either first cover the implant with sclera tissue and close and suture the sac or introduce the sterile implant directly into the void. If a sclera sac is employed windows can be cut through the tissue to coincide with the approximate position of attachment of the rectus muscles. In the event the patient's own sclera tissue is unavailable for use, sclera tissue can be obtained from a from a tissue bank.

After insertion of the orbital implant the muscles of the eye are attached either to the tissue covering the implant or sutured directly to the implant material. The attachment of the muscle to the implant is significantly enhanced by the subsequent vascularization of the porous surface of the sample by connective tissues surrounding the muscles. The muscles will provide motility to the implant after healing has taken place and the direct attachment and subsequent tissue ingrowth provides excellent motility to the implant. The surgeon closes the conjunctiva around the anterior portion of the implant and the area is allowed to heal. As the area heals, the tissue around the implant will vascularize and grow into the porous surface of the implant. Vascularization should be allowed to proceed until it penetrates the anterior surface of the implant to a depth of more than 6 mm.

After a few months the patient can be fitted with the ocular prosthesis and the coupling device is positioned and installed. Although some motility and cosmesis may be achieved by the simple insertion of the prosthesis over the tissue covering the orbital implant, these characteristics can be improved by coupling the prosthesis to the orbital implant. Coupling of prosthesis to the implant the can also help support the weight of the prosthesis and thereby reduce the pressure imposed by the prosthesis on the lower eyelid.

The coupling is made by insertion of the screw having a domed or rounded head as described above into the orbital implant. The head is shaped to conform to a cavity provided on the rear side of the ocular prosthesis. Using a template, the surgeon first determines the center of the implant in relation to the functional eye and marks the spot. It is recommended that the ocularlist prepare a template like the prosthetic eye with a though hole which indicates the optimum location for screw placement. At this location the surgeon first pierces the conjunctiva with a scalpel or needle to minimize trauma imposed by the drilling operation. Next the surgeon drills a pilot hole perpendicular to the anterior surface of the implant to a depth of 6 mm with the 1 mm drill bit. Preferably the pilot hole is drilled using a twist bit having a diameter of 1 mm and is comprised of 316 stainless steel. The cutting surface of the drill bit is preferably limited to the end of the bit. The bit should be pre-sterilized according to the sterilization policy of the institution at which the surgery occurs. Using a 1 mm drill bit significantly reduces the trauma to the conjunctiva during the drilling operation as contrasted with prior art drilling operations performed to situate a peg. The depth of the hole can be checked with a sterile needle. Any loose particles created by the drilling procedure can be rinsed away with an antibiotic solution.

The pilot hole, which has a diameter of approximately 1 mm (approximately ½ the diameter of the shank portion of the screw), extends through the conjunctiva and any tissue which has invaded the surface of the implant and into the interior of the implant. Next the screw is driven into the implant with a driver by the surgeon. The screw threads may be coated with a sterile antibiotic ointment prior to insertion in order to minimize the incidence of infection. The region of the screw where the threads are provided has a diameter which is slightly less than the pilot hole. As the screw is driven into the implant the threads engage female threads which are formed in the self-tapped hole by compressing the porous plastic material around the drilled hole. The ocular screw essentially engages the implant material in the same fashion as a wood screw engages wood. The screw is inserted into the implant until the bottom surface 34 of the screw head is even with the conjunctiva. The screw head should thus project above the conjunctiva just enough to allow secure mating with a socket created by the ocularist on the back of the ocular prosthesis. After the screw is inserted into the implant, the tissue surrounding the screw should again be allowed to heal before an appointment is scheduled with the ocularist. After the ocular screw has been positioned and the conjunctiva has healed to the doctors satisfaction, the prosthesis is ready to be coupled to the implant. The fitting of the prosthesis first involves first cutting out a section from the rear of the prosthesis at the approximate location of the head of the screw to make room for the entire screw head. With the patient sitting and looking straight ahead, a small amount of alginate is placed within the cut out section of the prosthesis. An impression is then made to show the location of the screw head in the socket.

A new mold is then be made from the alginate impression. Often the "screw head" portion of the mold will break off in the alginate. This does not present a problem since the location for the screw will still be evident. If the screw head, does not break, the ocularist should grind it down so only a small point remains to mark the location. Next, the previously cut out area is filled with alginate. Finally, a small depression in the rear of the prosthesis at the location of the screw is made by drilling at the location of the screw head. The depression should be just large enough to stay on the screw head when it is received in the socket. The rounded or domed head of the screw thus provides a round ball for the ocularist to mate with a matching socket on the prosthesis. The natural motion of the implant is directly transferred to the prosthesis by the screw head.

The foregoing description is of a preferred embodiment of the invention and other modifications can be made to the above described specific embodiments without departing from the spirit and scope of the invention, which is defined in the appended claims.

We claim:

1. An improved ocular implant assembly comprising a porous implant, an ocular prosthesis and an ocular screw, said screw having a head and a shank, said implant having an interconnected pore structure to allow for tissue ingrowth, and provided with a pilot hole having side walls and a diameter less than the diameter of the shank said screw, said shank having threads which engage said implant adjacent to said side walls of said pilot hole and said head is received in a complementary recess provided on a posterior side of said ocular prosthesis wherein said head thereby provides a mechanical coupling which both translates movement of said implant to said prosthesis and provides support to said prosthesis, said mechanical coupling providing a bridge from said interconnected pore structure to the external environment.

2. The implant assembly recited in claim 1 wherein said head of said screw has a domed shape.

3. The implant assembly recited in claim 1 wherein said head of said screw has a cylindrical shape.

4. The implant assembly recited in claim 1 wherein said head of said screw has engagement means to receive screw driving means.

5. The implant assembly recited in claim 4 wherein said engagement means comprises a square hole.

6. The implant assembly recited in claim 1 wherein said screw is self-tapping.

7. The implant assembly recited in claim 1 wherein said screw is comprised of titanium.

8. The implant assembly recited in claim 1 wherein said screw has threads which comprise a first and second region wherein said first region has a first thread pitch and said second region has a second thread pitch thereby comprising a variable thread pitch pattern wherein aid variable thread pitch pattern provides for a secure attachment of said screw to said implant.

9. An ocular coupling system comprising an ocular implant, ocular prosthesis and motility coupling link, said ocular implant further comprising a completely porous substrate having an exterior surface, said ocular implant having a porosity which allows for vascularization by human tissue, said ocular implant implanted in an orbit, covered with epithelial tissue and allowed to become vascularized from said external surface toward the interior of said ocular implant and thereby forming a vascularized region, said motility coupling link further comprising an elongate bioinert member having a first end which penetrates said epithelial covering of said orbital implant and said vascularized region and a second end which radially extends from said exterior surface of said ocular implant so that said coupling link forms a bridge from the interior environment of a human body to an external environment, said second end further having means to engage said ocular prosthesis.

10. The ocular coupling system as recited in claim 9 wherein said bioinert member further comprises a stable and permanently affixed member and further adheres to conjunctiva epithelial tissue around an outer circumference located at the anterior surface of said ocular implant and thereby forms a circumferential seal around said bioinert member at a location tangent with said anterior surface.

11. The invention as recited in claim 9 wherein said ocular implant comprises polyethylene.

12. The invention as recited in claim 9 wherein said bioinert member is comprised of titanium.

13. The invention as recited in claim 9 wherein said bioinert member further comprises a self-tapping screw.

14. The invention as recited in claim 13 wherein said screw is comprised of titanium.

15. The invention as recited in claim 9 wherein said porous ocular implant is monolithic.

16. The invention as recited in claim 9 wherein said bioinert member is a solid one-piece part.

* * * * *